US011153526B2

(12) United States Patent
Rechner et al.

(10) Patent No.: US 11,153,526 B2
(45) Date of Patent: *Oct. 19, 2021

(54) DETECTION OF PHOTOSENSITIVE TRIGGERS IN VIDEO CONTENT

(71) Applicant: International Business Machines Corporation, Armonk, NY (US)

(72) Inventors: Istvan Rechner, Budapest (HU); Zoltan Ponekker, Monor (HU); Patrik Egyed, Budapest (HU)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/850,462

(22) Filed: Apr. 16, 2020

(65) Prior Publication Data
US 2020/0244917 A1 Jul. 30, 2020

Related U.S. Application Data

(63) Continuation of application No. 16/170,466, filed on Oct. 25, 2018, now Pat. No. 10,742,923.

(51) Int. Cl.
*H04N 5/57* (2006.01)
*G06K 9/00* (2006.01)
(Continued)

(52) U.S. Cl.
CPC ........... *H04N 5/57* (2013.01); *G06K 9/00744* (2013.01); *G06K 9/4647* (2013.01); *A61B 5/4094* (2013.01)

(58) Field of Classification Search
CPC .............................. A61B 5/4094; G06K 9/4647
(Continued)

(56) References Cited

U.S. PATENT DOCUMENTS 7,880,815 B2 2/2011 Yeh et al.
8,443,304 B2 5/2013 Cragun et al.
(Continued)

FOREIGN PATENT DOCUMENTS

CN 1226863 C 11/2005
CN 101340511 B 10/2011
(Continued)

OTHER PUBLICATIONS

Ma et al., "Parallel scheme for real-time detection of photosensitive seizures", Comput Biol Med. Mar. 1, 2016, Abstract only, 2 pages.
(Continued)

*Primary Examiner* — John W Miller
*Assistant Examiner* — Omer Khalid
(74) *Attorney, Agent, or Firm* — Stosch Sabo

(57) ABSTRACT

Techniques for detecting epileptic triggers in video content by storing a first sequence of frames of a video stream in a first buffer. The technique can further comprise generating a second sequence of subframes and storing the second sequence of subframes in a second buffer. The technique can further comprise generating average intensity values for the second sequence of subframes in the second buffer and calculating intensity changes between consecutive subframes in the second sequence of subframes based on the average intensity values. The technique can further comprise determining that a number of intensity changes between consecutive subframes in the second sequence of subframes exceeds an oscillation threshold and tagging the frames in the first buffer corresponding to the subframes in the second buffer as hazardous.

20 Claims, 5 Drawing Sheets

(51) Int. Cl.
  *G06K 9/46* (2006.01)
  *A61B 5/00* (2006.01)
(58) Field of Classification Search
  USPC .......... 348/687, 61, 180, 255, 688, 673, 672
  See application file for complete search history.

(56) References Cited

U.S. PATENT DOCUMENTS

| | | |
|---|---|---|
| 9,036,977 B2 | 5/2015 | Patten et al. |
| 9,807,445 B2 | 10/2017 | Mountain |
| 10,013,952 B2 | 7/2018 | Tam |
| 10,621,950 B2 * | 4/2020 | Kumar ................. G09G 3/3648 |
| 10,742,923 B2 * | 8/2020 | Rechner ............... G06K 9/4647 |
| 10,911,797 B2 * | 2/2021 | Griffiths ......... H04N 21/234345 |
| 2004/0165084 A1 | 8/2004 | Yamamoto et al. |
| 2008/0232765 A1 | 9/2008 | Patten et al. |
| 2013/0169880 A1 * | 7/2013 | Ferguson ................. G06T 7/20 348/607 |
| 2015/0363928 A1 * | 12/2015 | Mestha .................... A61B 5/01 382/128 |
| 2016/0335750 A1 * | 11/2016 | Usman .................. H04N 19/86 |
| 2017/0311012 A1 | 10/2017 | Griffiths |

FOREIGN PATENT DOCUMENTS

| | | |
|---|---|---|
| GB | 2507729 A | 5/2014 |
| WO | 2015107880 A1 | 7/2015 |
| WO | 2018/063521 A1 | 4/2018 |

OTHER PUBLICATIONS

Mell et al., "The NIST Definition of Cloud Computing", Recommendations of the National Institute of Standards and Technology, Sep. 2011, 7 pages.

IBM, List of IBM Patents or Patent Applications Treated as Related, Apr. 9, 2020, 2 pages.

Rechner et al., "Detection of Photosensitive Triggers in Video Content", U.S. Appl. No. 16/170,466, filed Oct. 25, 2018.

\* cited by examiner

DETECTION OF PHOTOSENSITIVE TRIGGERS IN VIDEO CONTENT

BACKGROUND

The present disclosure relates to modifying video content, and, more specifically, to detecting epilepsy risks in video content.

Epilepsy is the fourth most common neurological disorder in the United States. It can affect people of all ages and is characterized by unpredictable seizures, although it can cause other health problems as well. A potential epileptic trigger is visual in nature and can be caused by exposure to flashing lights, strobe lights, and/or saturation changes. These photosensitive conditions can occur in videos. Creators of video content may be unaware of the potential epilepsy risk of various video scenes. Likewise, viewers with epilepsy may be unable to predict which scenes may include epileptic triggers.

SUMMARY

Aspects of the present disclosure are directed toward a computer-implemented method comprising storing a first sequence of frames of a video stream in a first buffer. The method can further comprise generating a second sequence of subframes corresponding to a first portion of respective frames in the first sequence of frames. The method can further comprise storing the second sequence of subframes in a second buffer. The method can further comprise generating average intensity values for respective subframes in the second sequence of subframes. The method can further comprise calculating intensity changes between consecutive subframes in the second sequence of subframes based on the average intensity values. The method can further comprise determining that a number of intensity changes between consecutive subframes in the second sequence of subframes exceeds an oscillation threshold, where respective intensity changes in the number of intensity changes exceed an amplitude threshold. The method can further comprise tagging frames in the first sequence of frames as containing an epileptic trigger in response to determining that the number of intensity changes between consecutive subframes in the second sequence of subframes exceeds the oscillation threshold.

Further aspects of the present disclosure are directed toward a system and computer program product with functionality similar to the functionality discussed above regarding the computer-implemented method. The present summary is not intended to illustrate each aspect of, every implementation of, and/or every embodiment of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
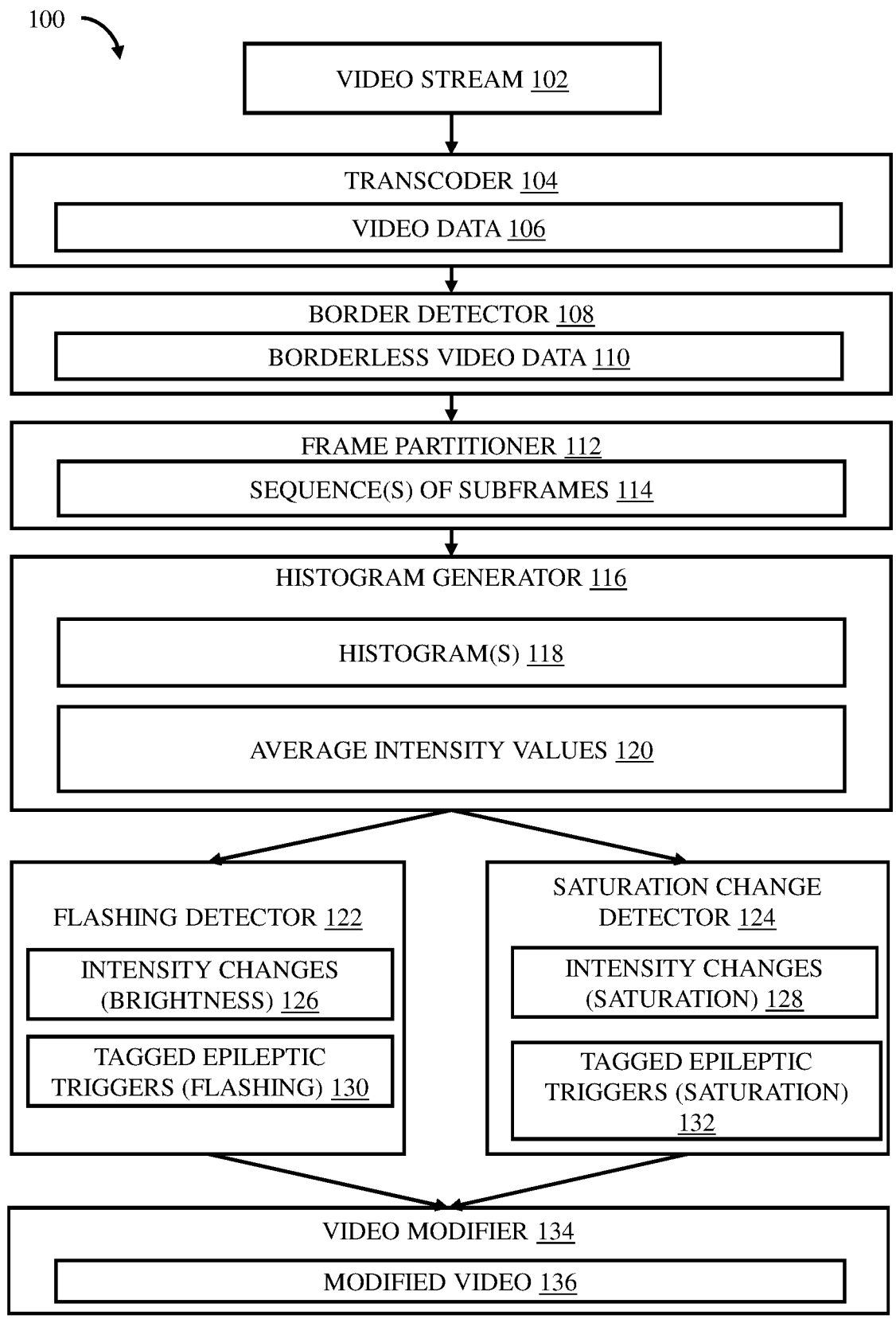
FIG. 1 illustrates a block diagram of an example video modification system, according to embodiments of the present disclosure.

While the present disclosure is amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the spirit and scope of the present disclosure.

DETAILED DESCRIPTION

Aspects of the present disclosure are directed toward modifying video content, and, more specifically, to removing epilepsy risks from video content. While not limited to such applications, aspects of the present disclosure may be better understood in light of the aforementioned context.

Video content containing epileptic triggers is a health hazard. Nonetheless, many people may be unaware of the video characteristics that constitute epileptic triggers. Furthermore, viewers with epilepsy are unable to preview video content without risking an epileptic seizure. Thus, there is a need to automatically identify video content containing epileptic triggers and modify video content to remove epileptic triggers.

Aspects of the present disclosure improve the technology of automatically detecting epileptic triggers in video content. For example, aspects of the present disclosure use subframes (e.g., a portion of a full frame) to identify epileptic triggers. This is beneficial compared to methods using an entire frame to detect epileptic triggers. Compared to methods that utilize an entire frame, aspects of the present disclosure are more efficient. Using subframes reduces the amount of processing power required to detect and tag epileptic triggers. For example, numerous sequences of subframes can be processed in parallel rather than a sequence of full frames. Because each sequence of subframes contains less data than a sequence of full frames, aspects of the present disclosure can realize reduced computational costs. Thus, aspects of the present disclosure realize at least improved processing performance (relative to strategies analyzing an entire frame).

As another example, aspects of the present disclosure analyze sequences of subframes spanning multiple seconds of video content, thereby identifying epileptic triggers that may not be identifiable between any two consecutive frames, but may be identified when viewed with several seconds worth of frames (e.g., 150 frames spanning 5 seconds of video content). Thus, aspects of the present disclosure can detect epileptic triggers that would otherwise go undetected using methods relying exclusively on paired-frame analysis.

As yet another example, aspects of the present disclosure utilize subframe average values (e.g., average luma values, average hue values, average saturation values, and/or average luminance values, etc.) to detect intensity changes rather than individual pixel values (e.g., minimum/maximum pixel values). Compared to methods relying on individual pixels, aspects of the present disclosure reduce false positives. For example, an epileptic trigger requires a substantial portion of the screen (e.g., approximately 25%) to undergo rapid intensity changes. Methods that rely on individual pixels may identify rapid intensity changes in a single pixel as an epileptic trigger. However, in reality, such a localized intensity change does not constitute an epileptic trigger. Thus, aspects of the present disclosure utilizing subframe average intensity values can exhibit increased accuracy (e.g., reduced false positives) relative to techniques relying on individual pixel values.

As still another example, aspects of the present disclosure increase accuracy by using both amplitude (e.g., average intensity changes) and frequency (e.g., oscillations per period of time) to identify epileptic triggers. Utilizing both amplitude and frequency is an improvement compared to strategies relying on either amplitude changes without frequency requirements, or frequency values without amplitude requirements, to detect epileptic triggers. Utilizing both amplitude thresholds and frequency thresholds improves accuracy by removing false positives associated with large amplitude changes with insufficient frequency (e.g., a single intense flash) or false positives associated with a high frequency and a low amplitude (e.g., muted flashing).

Further aspects of the present disclosure result in improved epileptic trigger mitigation at least insofar as the present disclosure utilizes the improved detection techniques discussed above to automatically modify video content to indicate locations of, and/or durations of, epileptic triggers. Some embodiments remove epileptic triggers from the video content. Aspects of the present disclosure can remove epileptic triggers by overwriting video data associated with frames identified as containing an epileptic trigger. The overwritten video data can result in changes in brightness, hue, saturation, color, or other aspects of the video data that reduces the epileptic trigger.

Thus, aspects of the present disclosure improve the technology of automated epileptic trigger detection in video content. Further aspects of the present disclosure improve the technology of epileptic trigger removal in video content. The aforementioned advantages are example advantages, and aspects of the present disclosure can exist that realize all, some, or none of the aforementioned advantages while remaining within the spirit and scope of the present disclosure.

FIG. 1 illustrates an example video modification system 100, according to some embodiments of the present disclosure. Video modification system 100 can receive video stream 102 at transcoder 104.

Video stream 102 can be digital video data having data in a video coding format (e.g., H.263, H.264, Dirac, MPEG-1, MPEG-2, MPEG-4, Windows Media Video, RealVideo, VP6, VP8, VP9, etc.). The video stream 102 can optionally include audio data in an audio coding format, synchronization information, subtitles, and/or metadata. Video stream 102 can be associated with a file extension such as, but not limited to, WebM (.webm), Windows Media Video (.wmv), Ogg Video (.ogv), Audio Video Interleave (AVI) (.avi), QuickTime (.mov), Flash Video or F4V (.flv), Matroska (.mkv), Dirac (.drc), Graphic Interchange Format (GIF) (.gif), Video Alternative to GIF (.gifv), raw video format (.yuv), RealMedia (.rm), RealMedia Variable Bitrate (.rmvb), Advanced Systems Format (.asf), MPEG (.mp4, .m4v, .mpg, .mpeg, .m2v, .m4v), Nullsoft Streaming Video (.nsv), or a different file extension.

Video stream 102 can include a series of frames and an associated frame rate (which can be expressed in frames per second (FPS)). Example FPS values can be, but are not limited to, 16, 24, 30, 48, 50, 60, 120, 240, 300, or a different FPS value. In some embodiments, the frame rate is between 30 FPS and 120 FPS, inclusive. In some embodiments, FPS can be dynamic, such as applications where FPS values, resolution values, or other video attributes are dynamically modified based on available bandwidth, cache, or other factors.

In some embodiments, video stream 102 is a sequence of frames, where the sequence of frames refers to time-adjacent (e.g., consecutive, sequential) frames in the video stream 102. However, consecutive frames need only be consecutive with respect to other frames included in video stream 102. For example, to expedite processing, video stream 102 can exclude some frames from the original video data. Thus, two frames in video stream 102 may be consecutive compared to other frames in video stream 102, but may be separated by one or more frames when compared to the original video data.

In some embodiments, the video stream 102 is of controlled size (e.g., 150 frames). In other embodiments, where video stream 102 exceeds a controlled size, the video stream 102 can be segmented into controlled sizes by flashing detector 122 and/or saturation change detector 124 (discussed hereinafter).

Transcoder 104 can be any transcoding system capable of digital-to-digital conversion from one encoding to another. Transcoder 104 ingests video stream 102 and generates frame-by-frame timestamps, YUV data, RGB (red, green, blue) data, and/or HSL (hue, saturation, lightness) data in video data 106. Video data 106 is input from transcoder 104 to border detector 108.

Border detector 108 removes borders from video data 106 by, for example, removing black frames, borders, bands, or other portions of video data 106 that are irrelevant for identifying and/or removing epileptic triggers from video stream 102. Removing borders can advantageously make the remaining processes more efficient (e.g., reduced storage requirements, reduced processing requirements) without sacrificing precision or accuracy in detecting epileptic triggers. For example, black borders surrounding video stream 102 do not contribute to epileptic risks as the border color, brightness, intensity, and/or saturation do not change throughout a video. Furthermore, aspects of the present disclosure use average intensity values of subframes, and a subframe including a border portion may have its average values inappropriately weighted by a static black border. Border detector 108 generates borderless video data 110.

Borderless video data 110 is input to frame partitioner 112. Frame partitioner 112 defines subframes. In some embodiments, frame partitioner 112 defines subframes comprising at least 25% of the borderless video data 110, between 25%-50% of the borderless video data 110, or less than 25% of the borderless video data 110. In some embodiments, individual subframes comprise squares having a width equal to a height. In other embodiments, individual subframes comprise rectangles having a width different from a height of the rectangle. In some embodiments, 4, 16, 64, 128, 256, or a different number of partially overlapping regions (e.g., sharing one or more pixels between two or more regions) or non-overlapping regions (e.g., no shared pixels between any pair of regions) are defined. Frame partitioner 112 generates a sequence of subframes 114, where different subframes corresponds to a same region of different full frames in the video stream 102.

As an example, for a 1920 pixel width×1080 pixel height frame, there could be a 16×16 grid of 256 non-overlapping subframes, where each subframe includes dimensions of 120 pixels width×67.5 pixel height (where the pixel height may be rounded to a whole number, as appropriate). Although the aforementioned example includes 256 subframes, more or fewer subframes are possible. Although the aforementioned example includes 256 equally sized subframes, differently sized subframes are also possible. Although the aforementioned example includes non-overlapping subframes, overlapping subframes are possible.

In such an example, frame partitioner 112 can generate a separate sequence of subframes 114 for each series of frames in video stream 102 corresponding to a same subframe region. Continuing the example used above, frame partitioner 112 can generate 256 sequences of subframes 114.

Thus, sequence of subframes 114 includes a plurality of sequences of subframes, where each sequence of subframes corresponds to a same region in a plurality of sequential frames from the video stream 102 (e.g., if video stream 102 includes 150 frames, and a respective subframe area corresponds to a portion A1 of a frame, then a respective sequence of subframes includes the portion A1 of each frame of the 150 frames). For clarity, a single sequence of subframes 114 is discussed hereafter; however, it is to be understood that embodiments include parallel processing of multiple sequences of subframes 114 consistent with the processing described below.

Sequence of subframes 114 is input to histogram generator 116. Histogram generator 116 generates one or more histograms 118 for each subframe in sequence of subframes 114. Histograms 118 can include histograms based on any one of, or any combination of, YUV data, HSL data, and/or RGB data in sequence of subframes 114. As an example, an R histogram corresponding to RGB data for a first subframe can include an x-axis having R-values between 0 and 255 and a y-axis denoting a pixel count corresponding to a number of pixels in the first subframe having each R-value on the x-axis. As an example, if three pixels in the first subframe have an R-value of 122, then the x-value in the R histogram corresponding to 122 can have a y-value of three.

Histogram generator 116 can generate a variety of histograms 118 including, but not limited to, luma histograms (e.g., using a Y component of YUV data), hue histograms, saturation histograms, and/or luminance histograms using HSL data, and R histograms, G histograms, and/or B histograms using RGB data.

In some embodiments, the range of each histogram (e.g., the y-value range) is normalized between 0 and 1, inclusive. Normalizing histogram values can contribute to simplified processing.

Histogram generator 116 further generates average intensity values 120. In some embodiments, average intensity values 120 are based on data in histograms 118. Average intensity values 120 can include an average value for all of, a majority of, or a portion of pixels in a subframe in sequence of subframes 114, where the value corresponds to data such as, but not limited to, YUV data, HSL data, and/or RGB data. For example, one average intensity value can be an average of each Y value (e.g., luma) for each pixel in a first subframe in the sequence of subframes 114. The aforementioned example can likewise occur for hue values, saturation values, luminance values, red values, green values, blue values, or other values.

Although the term "histogram" is used herein, it is not to be construed as limiting. For example, a histogram can refer to data which may or may not be in chart format and includes information such as a subframe identifier (e.g., identifying a region of a full frame the subframe corresponds to, and further identifying a location (e.g., a timestamp) relative to other subframes in a sequence of subframes) and intensity values (e.g., from YUV data, HSL data, and/or RGB data) for each of, a majority of, or some of the pixels in the identified subframe. Such data can be stored in a histogram, however, the data can likewise be stored in alternative data storage formats such as, but not limited to, vectors, matrices, tables, charts, plots, and other data formats.

Histogram generator 116 inputs one or more of histograms 118 and/or average intensity values 120 into flashing detector 122 and saturation change detector 124.

Flashing detector 122 calculates intensity changes 126 related to brightness between subframes in the sequence of subframes 114 using differences in average intensity values 120 between consecutive subframes in the sequence of subframes 114. As an example, flashing detector 122 can calculate intensity changes 126 between consecutive subframes in sequence of subframes 114 using average intensity values 120 corresponding to luma (e.g., Y-component of YUV data) for subframes in the sequence of subframes 114.

In some embodiments, intensity changes 126 related to brightness satisfy an amplitude threshold and an oscillation threshold. In some embodiments, the amplitude threshold can be 0.8, or between 0.65 and 0.95 (e.g., where the amplitude threshold is a unitless number representing differences in normalized, average intensity values). In some embodiments, the oscillation threshold can be 20, or between 10 and 30 (e.g., wherein the oscillation threshold is a number representing a number of intensity changes 126 related to brightness above the amplitude threshold for a given sequence of subframes). Thus, intensity changes 126 related to brightness can include differences between average intensity values 120 above the amplitude threshold. In the event that the number of differences between average intensity values 120 above the amplitude threshold is above the oscillation threshold (e.g., 21 intensity changes above 0.8, where 0.8 is the amplitude threshold and 20 is the oscillation threshold), then one of, some of, or all of the subframes in sequence of subframes 114 can be tagged epileptic triggers 130 related to flashing.

Saturation change detector 124 calculates intensity changes 128 related to saturation between subframes in the sequence of subframes 114 using differences in average intensity values 120 between consecutive subframes in the sequence of subframes 114. As an example, saturation change detector 124 can calculate intensity changes 128 between consecutive subframes in sequence of subframes 114 using average intensity values 120 corresponding to HSL data for subframes in the sequence of subframes 114.

In some embodiments, intensity changes 128 related to saturation satisfy an amplitude threshold and an oscillation threshold. In some embodiments, the amplitude threshold can be 0.8, or between 0.65 and 0.95. In some embodiments, the oscillation threshold can be 5, or between 3 and 10. Thus, intensity changes 128 related to saturation can include differences between average intensity values 120 above the amplitude threshold. In the event that the number of differences between intensity values 120 above the amplitude threshold is above the oscillation threshold (e.g., 6 intensity changes above 0.8, where 0.8 is the amplitude threshold and 5 is the oscillation threshold), then one of, some of, or all of the subframes in sequence of subframes 114 can be tagged epileptic triggers 132 related to saturation.

In various embodiments, intensity changes 126 and 128 can be stored in a variety of formats. For example, intensity changes 126 and 128 can be derived from difference histograms based on histograms 118 and average intensity values 120. In such embodiments, the difference histograms can include an x-axis corresponding to respective frames in the sequence of subframes 114 and a y-axis corresponding to differences between average intensity values 120 for a given subframe indicated by the x-axis relative to a previous subframe on the x-axis.

In embodiments including difference histograms, each difference histogram indicates the differences between average intensity values 120 (e.g., luma, hue, saturation, and/or luminance values) and the direction of the change (e.g., bright to dark, dark to bright, saturated green to saturated red, saturated red to saturated green, etc.) for time-adjacent subframes corresponding to a same region of the full frame.

In other embodiments, intensity changes 126 and 128 can be stored in a vector, a matrix, a table, a database, or a different data structure useful for storing differences between consecutive average intensity values 120 for the sequence of subframes 114.

Flashing detector 122 and saturation change detector 124 can each use a buffer of modifiable ranges. For example, the buffer can comprise 5 seconds worth of subframes. For example, for a video with 30 frames per second (FPS), the buffer includes 150 subframes. In some embodiments, the buffer is an incrementing window so that each sequence of subframes can be analyzed. For example, a first buffer can be analyzed with subframes 1-150, and a second buffer can be analyzed with subframes 2-151. In other embodiments, the buffers partially overlap (e.g., one or more subframes in two or more buffers) or do not overlap (e.g., no shared subframes between any two buffers). In some embodiments, multiple buffers (corresponding to different regions defined by frame partitioner 112) are processed in parallel, thereby reducing processing time and increasing processing efficiency.

The amplitude threshold(s) and oscillation threshold(s) can be calculated based on clustering data from known (e.g., tagged) hazardous and non-hazardous video data. In various embodiments, amplitude thresholds for flashing and saturation changes can be the same or different (e.g., an amplitude threshold for flashing could be 0.85, whereas an amplitude threshold for saturation changes could be 0.75). In various embodiments, the oscillation threshold for flashing and saturation changes can be the same or different (e.g., an oscillation threshold for flashing could be 20, whereas an oscillation threshold for saturation changes could be 5).

Flashing detector 122 and saturation change detector 124 each tag hazardous frame sequences in tagged epileptic triggers 130 related to flashing and tagged epileptic triggers 132 related to saturation. In some embodiments, the tagging indicates a starting location (e.g., frame identifier, timestamp, etc.) and a duration of the epileptic trigger. Tagged epileptic triggers 130 and 132 can be provided to video modifier 134.

Video modifier 134 modifies the video stream 102 at locations marked by tagged epileptic triggers 130 and 132 to indicate, remove, and/or reduce flashing and/or saturation changes. Video modifier 134 can remove the tagged frames, remove a portion of the tagged frames (e.g., for a sequence of subframes 114 tagged by the flashing detector 122, removing only the darkened frames, thereby reducing the intensity of the flashing), or modify the existing frames (e.g., overwriting YUV, HSL, and/or RGB values to modify the intensity, saturation, color, and/or brightness of the frames) to reduce the hazardous portions of the video stream 102.

Video modifier 134 can store, output, transmit, or otherwise generate modified video 136. Modified video 136 can exhibit decreased epileptic hazards relative to video stream 102 (e.g., by including an indication of a location and duration of an epileptic trigger, and/or by removing an epileptic trigger). In some embodiments, video modifier 134 also modifies audio data, synchronization data, or other data that can result in an improved viewing experience of the modified video 136.

Although video modification system 100 is shown including both flashing detector 122 and saturation change detector 124 being used by video modifier 134, embodiments exist that utilize only one of flashing detector 122 or saturation change detector 124.

Although the transcoder 104, border detector 108, frame partitioner 112, histogram generator 116, flashing detector 122, saturation change detector 124, and video modifier 134 are shown as discrete components in video modification system 100, the aforementioned components need not be discrete hardware elements, but are rather intended to illustrate discrete functionality (e.g., processor-executable program instructions) that can be implemented on a single set of hardware or multiple sets of hardware. In some embodiments, video modification system 100 is implemented virtually, such that all of, or part of, the functionality discussed with respect to any of transcoder 104, border detector 108, frame partitioner 112, histogram generator 116, flashing detector 122, saturation change detector 124, and/or video modifier 134 is realized by one or more virtual machines in a distributed computing environment.

In embodiments where two or more of transcoder 104, border detector 108, frame partitioner 112, histogram generator 116, flashing detector 122, saturation change detector 124, and video modifier 134 reside on separate hardware platforms (e.g., distributed), the two or more components can be communicatively coupled by a permanent, semi-permanent, or intermittent physical or virtual network connection.

Figure 2:
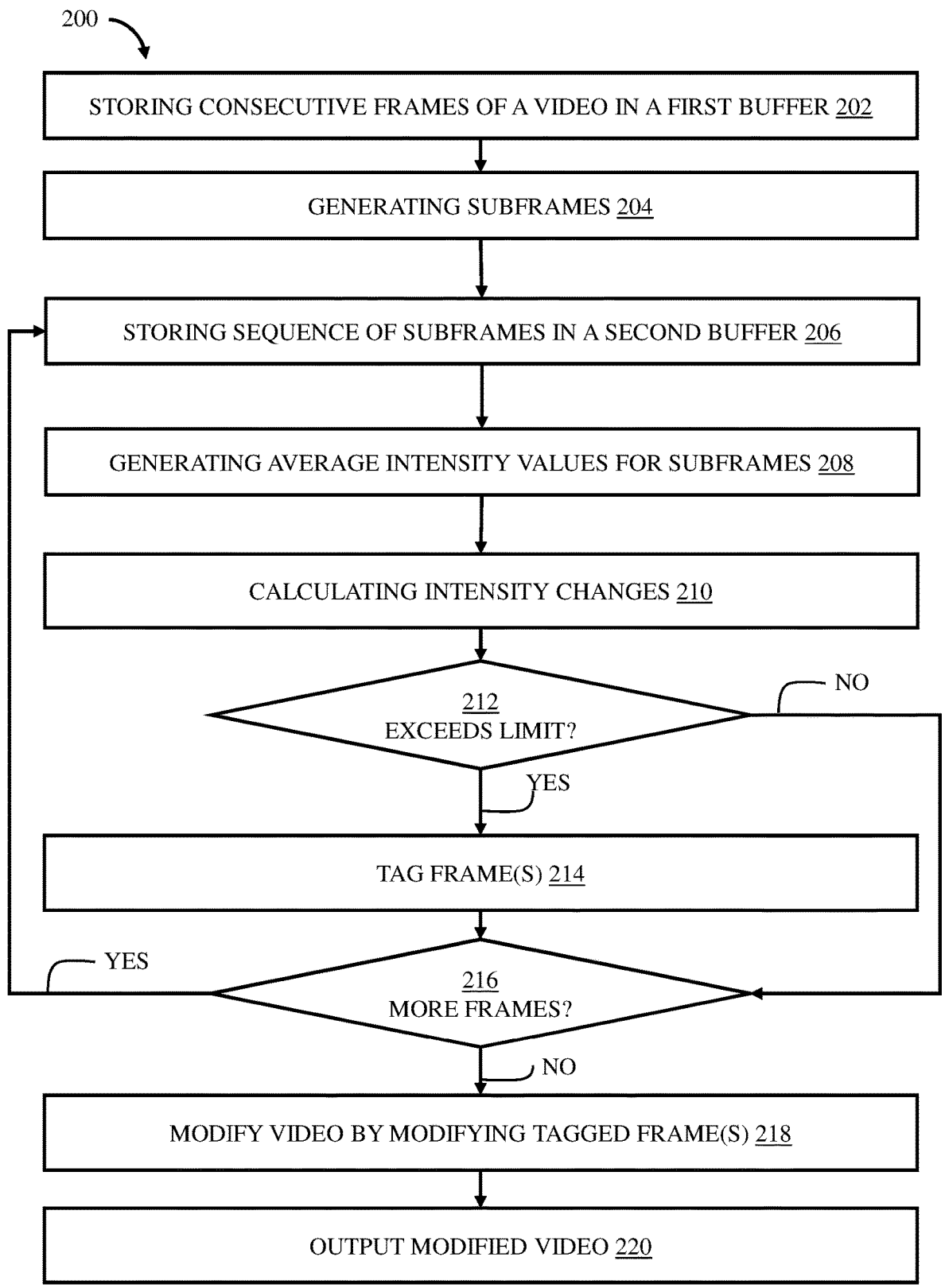
FIG. 2 illustrates a flowchart of an example method for detecting epileptic triggers in a video, according to embodiments of the present disclosure.

FIG. 2 illustrates a flowchart of an example method for detecting epileptic triggers in a video, according to embodiments of the present disclosure. The method 200 can be implemented by one or more processors, a video manager 300 of FIG. 3 (discussed hereinafter), one or more components of the video modification system 100 of FIG. 1, or a different configuration of hardware and software. In some embodiments, the computer-executable instructions for the method 200 are provided from a server to a client device such that the client device performs some of, or all of, the method 200 based on the computer-executable instructions. For clarity, the method 200 will be discussed as being implemented by a video manager.

In operation 202, the video manager stores a sequence of consecutive frames of a video stream in a first buffer. In some embodiments, the first buffer comprises frames corresponding to an interval of time (e.g., 1 second, 2 seconds, 3 seconds, 5 seconds, 10 seconds, etc.). The number of frames can be based on the interval of time and the FPS rate of the video. For example, the first buffer can include 150 frames corresponding to five seconds of a video at 30 FPS. In some embodiments, the first buffer comprises between 100 and 200 frames, inclusive.

The term "consecutive" should be understood to mean relative to other frames stored in the first buffer, rather than relative to all frames of the video data. For example, some embodiments may perform processing on every other frame of video data in order to reduce processing overhead. In such an example, consecutive frames in the first buffer may correspond to frames that are time-adjacent compared to other frames in the first buffer, but which may be separated by one or more frames when compared with the original video data.

As used herein, the term "buffer" refers generally to a region of a physical memory storage useful for temporarily storing data while it is undergoing processing, transmission, or otherwise being utilized. References to buffers can also apply to virtual buffers implemented in software applications.

Although not explicitly shown, various pre-processing can occur prior to operation 202. For example, the video manager can receive a video stream and extract data from the video stream (e.g., pixel data related to YUV data, HSL data, RGB data, etc.) using functionality similar to the functionality of transcoder 104 discussed in FIG. 1. Furthermore, the video manager can remove borders associated with the video stream (e.g., black borders) using functionality similar to the functionality of border detector 108 discussed in FIG. 1.

In operation 204, the video manager generates subframes corresponding to the portions of frames in the sequence of consecutive frames in the first buffer. The video manager can generate subframes by splitting respective frames into a plurality of regions. In various embodiments, the plurality of regions are equally sized regions (e.g., 100 pixels×100 pixels) or differently sized regions (e.g., a first set of regions 100 pixels×100 pixels, a second set of regions 200 pixels×50 pixels). In some embodiments, the video manager generates 4, 16, 32, 64, 128, 256, or a different number of regions for each frame with one subframe corresponding to each region of the plurality of regions in the frame. In some embodiments, each region comprises at least 25% of a screen area, less than 25% of a screen area, or between 25%-50%, inclusive, of the screen area. In various embodiments, respective regions partially overlap one another or do not overlap one another.

In operation 206, the video manager stores a sequence of consecutive subframes in a second buffer. For example, each frame can have four subframes. In such an example, four separate second buffers can be created to store each sequence of subframes. By storing sequences of subframes in separate second buffers, aspects of the present disclosure can perform parallel processing on the separate second buffers, thereby improving processing performance. Although four subframes were described in the previous example, aspects of the present disclosure can have more subframes, according to some embodiments. For example, there may be 4, 16, 32, 64, 128, 256, or a different number of subframes, with each respective sequence of subframes stored in a separate second buffer. For clarity, the remainder of the method 200 is described with respect to one second buffer storing a single sequence of subframes.

The sequence of subframes stored in the second buffer can have a number of subframes equal to or less than the number of frames in the sequence of frames stored in the first buffer.

In operation 208, the video manager generates average intensity values for subframes in the second buffer. The average intensity values can be based on, for example, YUV histograms, hue histograms, saturation histograms, luminance histograms, and/or RGB histograms using YUV, HSL, and/or RGB data from the video data. Each histogram can be used to calculate, for each subframe in the sequence of subframes, an average intensity value (e.g., luma value, hue value, saturation value, luminance value, etc.). The average intensity value can be derived from a plurality of pixel values in the subframe (e.g., all pixels in the subframe, a majority of pixels in the subframe, or a portion of the pixels in the subframe). In some embodiments, the average intensity values are normalized between 0 and 1, inclusive. As previously discussed, although histograms are discussed in operation 208, any appropriate data structure (e.g., vectors, tables, plots, etc.) can be used to store the data generated in operation 208.

In operation 210, the video manager determines respective sizes of respective intensity changes (e.g., bright to dark, dark to bright, saturated green to saturated red, saturated red to saturated green, etc.) in the subframes in the second buffer using the average intensity values generated in operation 208. As used herein, the phrases "intensity changes" and "differences between consecutive average intensity values" can be used interchangeably. Operation 210 can further include determining a number of intensity changes (e.g., oscillations). An oscillation can comprise a count corresponding to the number of intensity changes above an amplitude threshold.

Operation 210 can comprise calculating differences in average intensity values between time-adjacent (e.g., consecutive) subframes in the sequence of subframes. For example, for luma data, the intensity change can correspond to differences in average luma values between consecutive subframes. Each luma value change between consecutive subframes above an amplitude threshold can be counted as an intensity change (e.g., an oscillation).

Operation 210 can alternatively, or additionally, calculate differences between average HSL values and/or average RGB values in consecutive subframes of the sequence of subframes. The HSL data can be used to determine saturation changes. Each saturation change between consecutive subframes above an amplitude threshold can be counted as an intensity change (e.g., an oscillation).

In some embodiments, the amplitude threshold on a normalized scale for luma, hue, saturation, and/or luminance can be 0.8. As an example, a change from 1.0 average luma in a first subframe to 0.1 average luma in a sequential second subframe constitutes an intensity change of 0.9. In this example, the intensity change can be counted as an oscillation since it is above the amplitude threshold of 0.8. In other embodiments, the amplitude threshold can be between 0.65 and 0.95, inclusive.

In operation 212, the video manager compares the number of intensity changes calculated in operation 210 to an oscillation threshold. For example, the oscillation threshold for flashing can be 20. As another example, the oscillation threshold for saturation changes can be 5. Thus, more than one oscillation threshold can be used for different types of intensity changes (e.g., a first oscillation threshold for intensity changes derived from luma data, a second oscillation threshold for intensity changes derived from saturation data, etc.).

In the event that the video manager determines, in operation 212, that the limit is not exceeded (NO at operation 212), the method 200 can proceed to operation 216 (discussed in further detail hereinafter).

In the event that the video manager determines, in operation 212, that the limit is exceeded (YES at operation 212), the method 200 can proceed to operation 214.

In operation 214, the video manager tags the frames corresponding to the subframes in the second buffer as hazardous. The tagging can include an annotation identifying the frame as posing an epileptic risk and/or containing an epileptic trigger. In some embodiments, the tagging includes information regarding the number and size of various intensity changes calculated in operation 210. In some embodiments, the tagging includes a starting location and a duration of an epileptic trigger.

In operation 216, the video manager determines if there are more frames in the received video stream. If there are more frames (e.g., YES at operation 216), the video manager returns to operation 206 and stores a new sequence of consecutive subframes of the video stream in the second buffer. In some embodiments, the new sequence of consecutive subframes can be the previous sequence of subframes incremented by one (e.g., if the previous number of subframes was 151-300, the new number of subframes can be subframes 152-301). In some embodiments, the new sequence of consecutive subframes can overlap the previous number of frames by two or more subframes (e.g., if the previous number of subframes was 151-300, the new number of subframes can be subframes 300-449). In some embodiments, the new sequence of consecutive subframes does not overlap the previous number of subframes (e.g., if the previous number of subframes was 151-300, the new number of subframes can be 301-450). In other embodiments, different incrementing and/or overlapping schemes are used.

Although returning to operation 206 is shown, in other embodiments, the method 200 can instead return to operation 202 and store a new sequence of frames in a first buffer. Alternatively, the method 200 can return to operation 210 in embodiments where all average intensity values for the entire video stream have already been calculated. In such embodiments, the method 200 can calculate an updated number of oscillations above an amplitude threshold for a new sequence of subframes.

If the video manager determines are no more frames, or that the number of remaining frames is insufficient to fill the second buffer, (e.g., NO at operation 216), the video manager can proceed to operation 218.

In operation 218, the video manager modifies the video to mitigate epileptic triggers associated with the video. The video manager can modify the video by modifying at least the frames tagged in operation 214. The video manager can modify frames by removing frames and/or overwriting HSL, YUV, and/or RGB data associated with tagged frames. For example, the video manager can reduce the intensity of flashing in various tagged frames by modifying luma values associated with the tagged frames so that there is less difference between luma values in consecutive frames. As another example, the video manager can overwrite HSL data in the tagged frames to decrease the intensity of saturation changes between consecutive frames. In some embodiments, operation 218 modifies the video to include an indication that there is an epileptic trigger in the video. In some embodiments, the indication further identifies a time in the video at which the epileptic trigger occurs, and a duration of time that the epileptic trigger lasts. Other modifications are possible and fall within the spirit and scope of the present disclosure.

In operation 220, the video manager can output the modified video. Outputting the modified video can include saving the modified video to a tangible storage device. Outputting the modified video can include transmitting the modified video to a client device. Outputting the modified video can include publishing the modified video to a distributed storage system.

Figure 3:
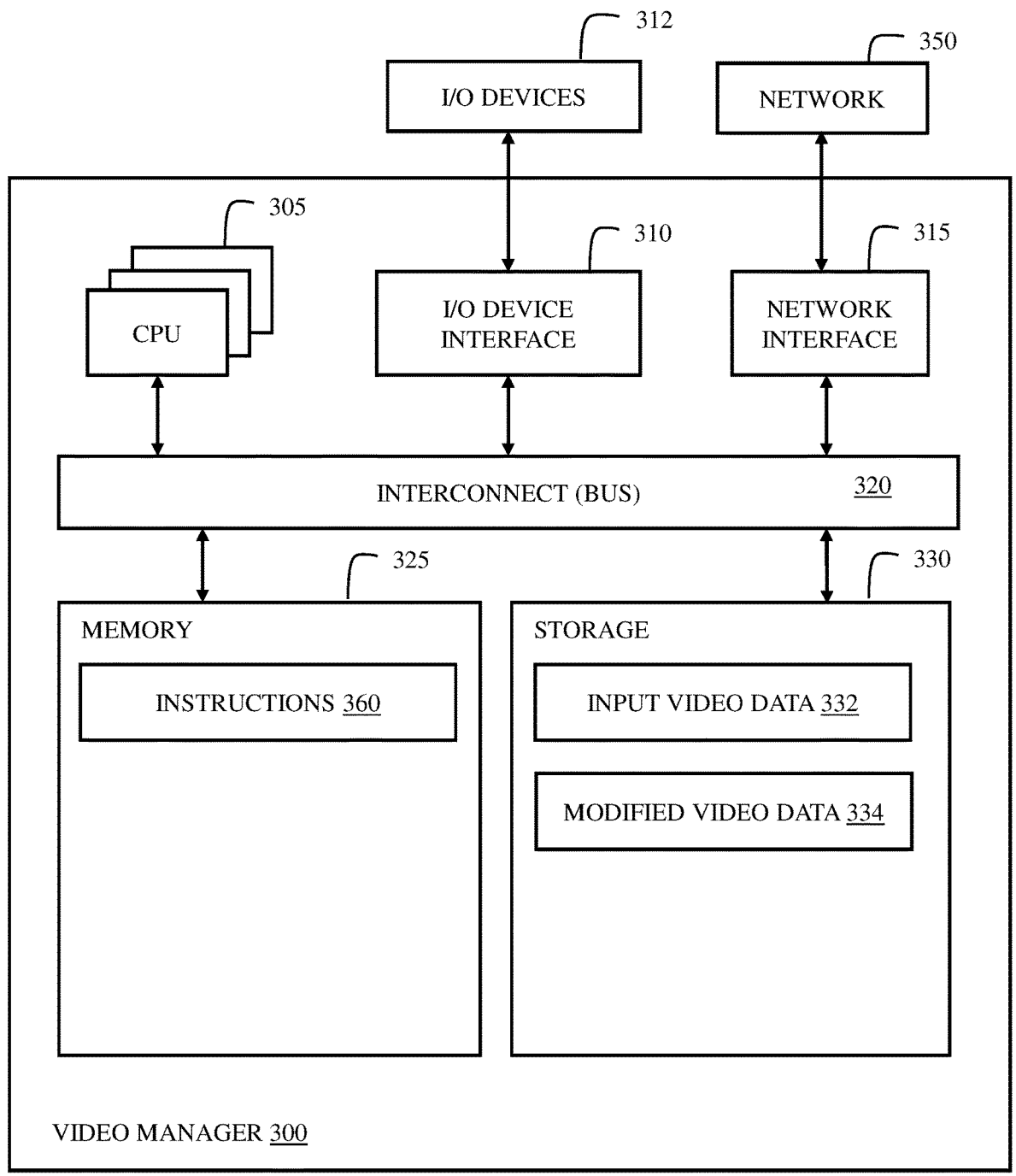
FIG. 3 illustrates a block diagram of an example video manager, in accordance with embodiments of the present disclosure.

FIG. 3 illustrates a block diagram of an example video manager 300 in accordance with some embodiments of the present disclosure. In various embodiments, video manager 300 can perform the method described in FIG. 2. In some embodiments, video manager 300 provides instructions for the method described in FIG. 2 to a client machine such that the client machine executes the method, or a portion of the method, based on the instructions provided by the video manager 300. In some embodiments, video manager 300 can execute operations in a physically constructed or virtually configured system in accordance with FIG. 1. In some embodiments, video manager 300 interfaces with a client machine to provide virtual services consistent with any portion of, or all of, the functionality discussed in FIG. 1.

The video manager 300 includes a memory 325, storage 330, an interconnect (e.g., BUS) 320, one or more CPUs 305 (also referred to as processors 305 herein), an I/O device interface 310, I/O devices 312, and a network interface 315.

Each CPU 305 retrieves and executes programming instructions stored in the memory 325 or storage 330. The interconnect 320 is used to move data, such as programming instructions, between the CPUs 305, I/O device interface 310, storage 330, network interface 315, and memory 325. The interconnect 320 can be implemented using one or more busses. The CPUs 305 can be a single CPU, multiple CPUs, or a single CPU having multiple processing cores in various embodiments. In some embodiments, a CPU 305 can be a digital signal processor (DSP). In some embodiments, CPU 305 includes one or more 3D integrated circuits (3DICs) (e.g., 3D wafer-level packaging (3DWLP), 3D interposer based integration, 3D stacked ICs (3D-SICs), monolithic 3D ICs, 3D heterogeneous integration, 3D system in package (3DSiP), and/or package on package (PoP) CPU configurations). Memory 325 is generally included to be representative of a random access memory (e.g., static random access memory (SRAM), dynamic random access memory (DRAM), or Flash). The storage 330 is generally included to be representative of a non-volatile memory, such as a hard disk drive, solid state device (SSD), removable memory cards, optical storage, or flash memory devices. In an alternative embodiment, the storage 330 can be replaced by storage area-network (SAN) devices, the cloud, or other devices connected to the video manager 300 via the I/O device interface 310 or a network 350 via the network interface 315.

In some embodiments, the memory 325 stores instructions 360 and the storage 330 stores input video data 332 and modified video data 334. However, in various embodiments, the instructions 360, input video data 332, and modified video data 334 are stored partially in memory 325 and partially in storage 330, or they are stored entirely in memory 325 or entirely in storage 330, or they are accessed over a network 350 via the network interface 315.

Instructions 360 can be processor-executable instructions for performing any portion of, or all of, any of the method of FIG. 2 and/or the functionality discussed in FIG. 1. Input video data 332 can be consistent with video stream 102 of FIG. 1 or an input video stream used in the method 200 of FIG. 2. Input video data can have intensity changes (e.g., brightness changes, saturation changes, etc.) that may pose an epileptic risk.

Modified video data 334 can be consistent with modified video 136 of FIG. 1 or an output of operation 220 of FIG. 2. Modified video data 334 can comprise video data that, when played to an audience, does not pose any epileptic risks as a result of intensity changes (e.g., brightness changes, saturation changes, etc.), and/or provides a notification if such an epileptic risk does exist.

In various embodiments, the I/O devices 312 include an interface capable of presenting information and receiving input. For example, I/O devices 312 can present information to a user interacting with video manager 300 and receive input from the user.

Video manager 300 is connected to the network 350 via the network interface 315. Network 350 can comprise a physical, wireless, cellular, or different network.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
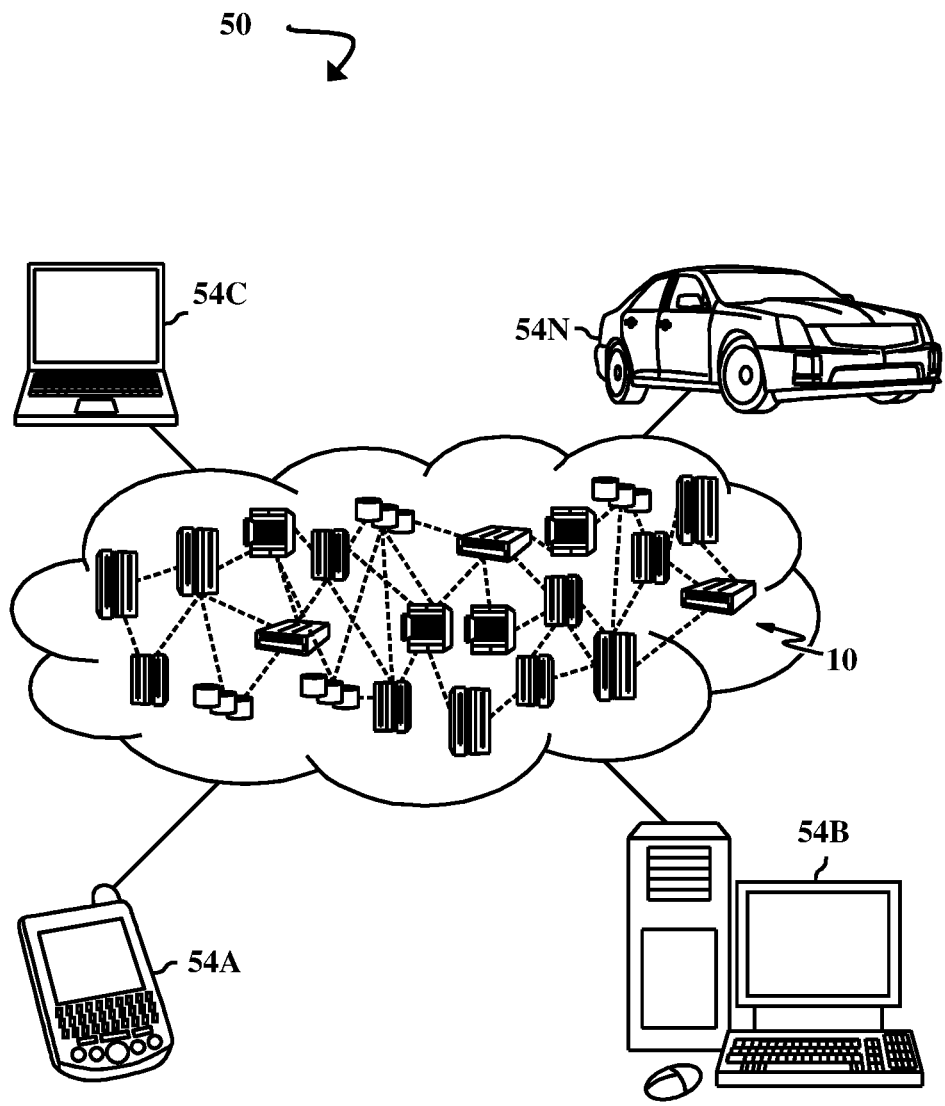
FIG. 4 depicts a cloud computing environment, according to some embodiments of the present disclosure.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
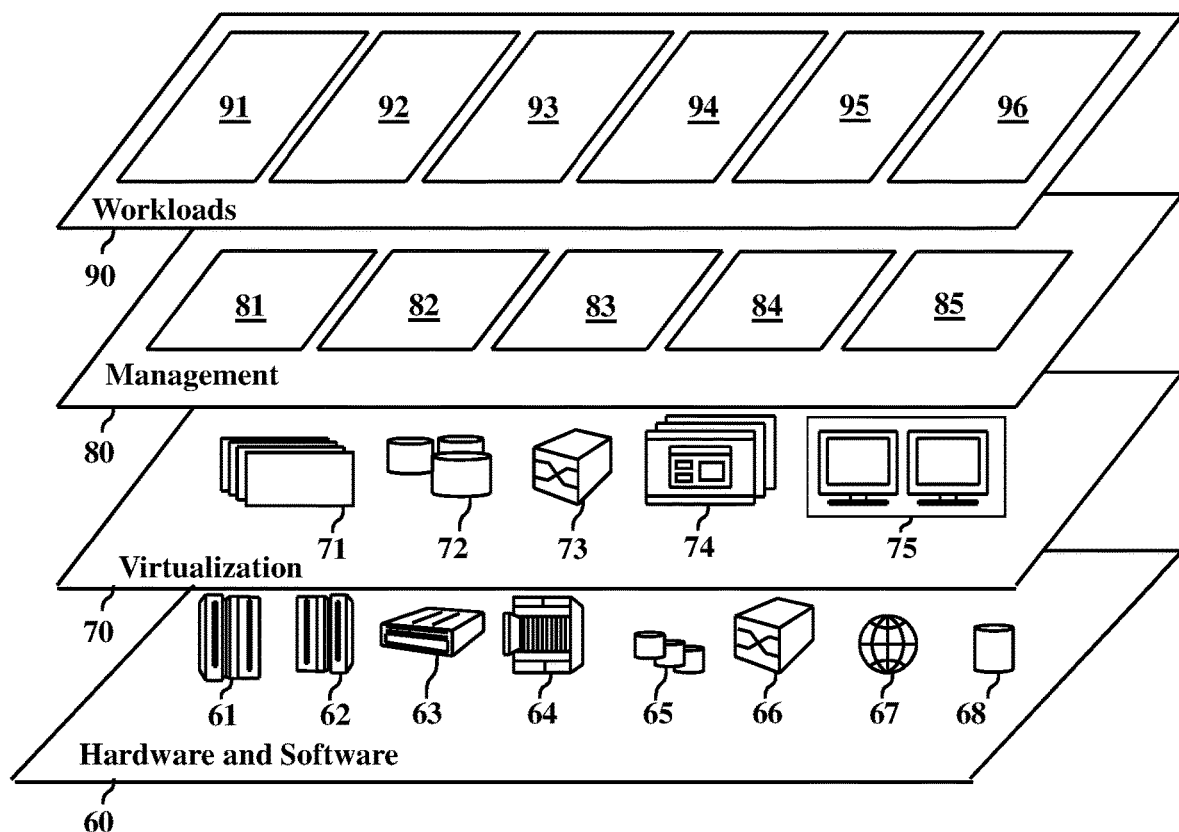
FIG. 5 depicts abstraction model layers, according to some embodiments of the present disclosure.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and video processing 96.

For clarity, one embodiment of the present disclosure will now be described in detail. The embodiment includes storing a first sequence of frames of a video stream in a first buffer and generating a second sequence of subframes corresponding to a first portion of respective frames in the first sequence of frames. The embodiment includes storing the second sequence of subframes in a second buffer. The embodiment includes generating average intensity values for respective subframes in the second sequence of subframes. The embodiment includes calculating intensity changes between consecutive subframes in the second sequence of subframes based on the average intensity values. The embodiment includes determining that a number of intensity changes between consecutive subframes in the second sequence of subframes exceeds an oscillation threshold, where respective intensity changes in the number of intensity changes exceed an amplitude threshold. The embodiment includes tagging frames in the first sequence of frames as containing an epileptic trigger in response to determining that the number of intensity changes between consecutive subframes in the second sequence of subframes exceeds the oscillation threshold.

A second embodiment including the aspects discussed in the first embodiment further includes generating a third sequence of subframes corresponding to a second portion of respective frames in the first sequence of frames.

A third embodiment including the aspects discussed in the second embodiment further includes the second portion partially overlapping the first portion.

A fourth embodiment including the aspects discussed in the second embodiment further includes the second portion being equal in size to the first portion.

A fifth embodiment including the aspects discussed in the first embodiment includes the first portion of each frame in the first sequence of frames comprising between 25% and 50%, inclusive, of an area of a respective frame in the first sequence of frames.

A sixth embodiment including the aspects discussed in the first embodiment includes removing respective borders of respective frames in the first sequence of frames.

A seventh embodiment including the aspects discussed in the first embodiment includes the average intensity values comprising average luma values for respective subframes in the second sequence of subframes.

An eighth embodiment including aspects discussed in the seventh embodiment includes a first average luma value based on luma values of a majority of pixels in a first subframe of the second sequence of subframes.

A ninth embodiment including the aspects discussed in the first embodiment further includes the average intensity values comprising average hue values, average saturation values, and average luminance values for respective subframes in the second sequence of subframes.

A tenth embodiment including the aspects discussed in the first embodiment further includes modifying respective frames in the first sequence of frames to mitigate the epileptic trigger, and outputting a modified video stream in response to modifying respective frames in the first sequence of frames.

An eleventh embodiment including the aspects discussed in the tenth embodiment includes overwriting luma values of pixels in the first portion of respective frames in the first sequence of frames.

A twelfth embodiment including the aspects discussed in the tenth embodiment includes overwriting a characteristic of respective frames in the first sequence of frames, where the characteristic is selected from the group consisting of: hue, saturation, and luminance.

A thirteenth embodiment including the aspects discussed in the first embodiment, where an intensity change comprises a change in average brightness values between consecutive subframes in the second sequence of subframes.

A fourteenth embodiment including the aspects discussed in the first embodiment, where an intensity change comprises a change in average saturation values between consecutive subframes in the second sequence of subframes.

A fifteenth embodiment including the aspects discussed in the first embodiment, wherein the second sequence of subframes comprises between 3 seconds and 8 seconds of the video stream, inclusive.

A sixteenth embodiment including the aspects discussed in the first embodiment, where the second sequence of subframes comprises between 100 subframes and 200 subframes, inclusive.

A seventeenth embodiment including the aspects discussed in the first embodiment, where the oscillation threshold is between 5 and 20, inclusive, and where intensity changes are normalized between 0 and 1, inclusive, and where the amplitude threshold is between 0.65 and 0.95, inclusive.

An eighteenth embodiment where instructions for one of, or a combination of, the above embodiments are stored in a computer-readable storage medium in a server data processing system, and where the instructions are downloaded over a network to a remote data processing system for use in a computer-readable storage medium with the remote system.

The aforementioned embodiments are not necessarily mutually exclusive, and different embodiments can be combined in different combinations other than the combinations explicitly discussed unless the plain meaning of the text clearly indicates otherwise. Furthermore, the aforementioned embodiments are example embodiments, and do not represent all aspects of the present disclosure, nor do they represent all limitations potentially attributable to the present disclosure, nor do they require each limitation discussed in any single embodiment in order to fall within the spirit and scope of the present disclosure, nor do they imply any limitation to any particular statutory class that may be claimed, now or in the future.

Embodiments of the present invention can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or subset of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While it is understood that the process software (e.g., any of the instructions stored in instructions 360 of FIG. 3 and/or any software configured to perform any subset of the method described with respect to FIG. 2, or to implement the functionality discussed in FIG. 1, in whole or in part) can be deployed by manually loading it directly in the client, server, and proxy computers via loading a storage medium such as a CD, DVD, etc., the process software can also be automatically or semi-automatically deployed into a computer system by sending the process software to a central server or a group of central servers. The process software is then downloaded into the client computers that will execute the process software. Alternatively, the process software is sent directly to the client system via e-mail. The process software is then either detached to a directory or loaded into a directory by executing a set of program instructions that detaches the process software into a directory. Another alternative is to send the process software directly to a directory on the client computer hard drive. When there are proxy servers, the process will select the proxy server code, determine on which computers to place the proxy servers' code, transmit the proxy server code, and then install the proxy server code on the proxy computer. The process software will be transmitted to the proxy server, and then it will be stored on the proxy server.

Embodiments of the present invention can also be delivered as part of a service engagement with a client corporation, nonprofit organization, government entity, internal organizational structure, or the like. These embodiments can include configuring a computer system to perform, and deploying software, hardware, and web services that implement, some or all of the methods described herein. These embodiments can also include analyzing the client's operations, creating recommendations responsive to the analysis, building systems that implement subsets of the recommendations, integrating the systems into existing processes and infrastructure, metering use of the systems, allocating expenses to users of the systems, and billing, invoicing (e.g., generating an invoice), or otherwise receiving payment for use of the systems.

The terminology used herein is for the purpose of describing particular embodiments only and is not intended to be limiting of the various embodiments. As used herein, the singular forms "a," "an," and "the" are intended to include the plural forms as well, unless the context clearly indicates otherwise. It will be further understood that the terms "includes" and/or "including," when used in this specification, specify the presence of the stated features, integers, steps, operations, elements, and/or components, but do not preclude the presence or addition of one or more other features, integers, steps, operations, elements, components, and/or groups thereof. In the previous detailed description of example embodiments of the various embodiments, reference was made to the accompanying drawings (where like numbers represent like elements), which form a part hereof, and in which is shown by way of illustration specific example embodiments in which the various embodiments can be practiced. These embodiments were described in sufficient detail to enable those skilled in the art to practice the embodiments, but other embodiments can be used and logical, mechanical, electrical, and other changes can be made without departing from the scope of the various embodiments. In the previous description, numerous specific details were set forth to provide a thorough understanding the various embodiments. But, the various embodiments can be practiced without these specific details. In other instances, well-known circuits, structures, and techniques have not been shown in detail in order not to obscure embodiments.

Different instances of the word "embodiment" as used within this specification do not necessarily refer to the same embodiment, but they can. Any data and data structures illustrated or described herein are examples only, and in other embodiments, different amounts of data, types of data, fields, numbers and types of fields, field names, numbers and types of rows, records, entries, or organizations of data can be used. In addition, any data can be combined with logic, so that a separate data structure may not be necessary. The previous detailed description is, therefore, not to be taken in a limiting sense.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present disclosure has been described in terms of specific embodiments, it is anticipated that alterations and modification thereof will become apparent to the skilled in the art. Therefore, it is intended that the following claims be interpreted as covering all such alterations and modifications as fall within the true spirit and scope of the disclosure.

What is claimed is:

1. A computer-implemented method comprising:
storing a sequence of subframes in a buffer, wherein the sequence of subframes comprise portions of a plurality of frames of video data;
generating average intensity values for respective subframes in the sequence of subframes;
calculating a plurality of intensity changes between consecutive subframes in the sequence of subframes based on the average intensity values;
determining that each of the plurality of intensity changes exceeds an amplitude threshold;
determining that the plurality of intensity changes exceeds an oscillation threshold; and
modifying respective frames corresponding to the sequence of subframes to mitigate an epileptic trigger in the video data.

2. The method according to claim 1, wherein the average intensity values comprise average luma values for respective subframes in the sequence of subframes.

3. The method according to claim 2, wherein a first average luma value is based on luma values of a majority of pixels in a first subframe of the sequence of subframes.

4. The method according to claim 1, wherein the average intensity values comprise average hue values, average saturation values, and average luminance values for respective subframes in the sequence of subframes.

5. The method according to claim 1, further comprising:
outputting modified video data in response to modifying respective frames corresponding to the sequence of subframes.

6. The method according to claim 5, wherein modifying respective frames comprises overwriting luma values of pixels in respective subframes of the sequence of subframes.

7. The method according to claim 5, wherein modifying respective frames comprises overwriting a characteristic of respective subframes in the sequence of subframes, wherein the characteristic is selected from the group consisting of: hue, saturation, and luminance.

8. The method according to claim 1, wherein an intensity change comprises a change in average brightness between consecutive subframes in the sequence of subframes.

9. The method according to claim 1, wherein an intensity change comprises a change in average saturation between consecutive subframes in the sequence of subframes.

10. The method according to claim 1, wherein the sequence of subframes comprises between 3 seconds and 8 seconds of a video stream, inclusive.

11. The method according to claim 1, wherein the sequence of subframes comprises between 100 subframes and 200 subframes, inclusive.

12. The method according to claim 1, wherein the oscillation threshold is between 5 and 20, inclusive, wherein average intensity values are between 0 and 1, inclusive, and wherein the amplitude threshold is between 0.65 and 0.95, inclusive.

13. A system comprising:
one or more processors; and
one or more computer-readable storage media storing program instructions which, when executed by the one or more processors, are configured to cause the one or more processors to perform a method comprising:
storing a sequence of subframes in a buffer, wherein the sequence of subframes comprise portions of a plurality of frames of video data;
generating average intensity values for respective subframes in the sequence of subframes;
calculating a plurality of intensity changes between consecutive subframes in the sequence of subframes based on the average intensity values;
determining that each of the plurality of intensity changes exceeds an amplitude threshold;
determining that the plurality of intensity changes exceeds an oscillation threshold; and
modifying respective frames corresponding to the sequence of subframes to mitigate an epileptic trigger in the video data.

14. The system according to claim 13, the method further comprising:
outputting modified video data in response to modifying respective frames corresponding to the sequence of subframes.

15. The system according to claim 14, wherein modifying respective frames comprises overwriting luma values of pixels in respective subframes of the sequence of subframes.

16. The system according to claim 14, wherein modifying respective frames comprises overwriting a characteristic of respective subframes in the sequence of subframes, wherein the characteristic is selected from the group consisting of: hue, saturation, and luminance.

17. A computer program product comprising one or more computer readable storage media, and program instructions collectively stored on the one or more computer readable storage media, the program instructions comprising instructions configured to cause one or more processors to perform a method comprising:
storing a sequence of subframes in a buffer, wherein the sequence of subframes comprise portions of a plurality of frames of video data;
generating average intensity values for respective subframes in the sequence of subframes;
calculating a plurality of intensity changes between consecutive subframes in the sequence of subframes based on the average intensity values;
determining that each of the plurality of intensity changes exceeds an amplitude threshold;
determining that the plurality of intensity changes exceeds an oscillation threshold; and
modifying respective frames corresponding to the sequence of subframes to mitigate an epileptic trigger in the video data.

18. The computer program product according to claim 17, the method further comprising:
outputting modified video data in response to modifying respective frames corresponding to the sequence of subframes.

19. The computer program product according to claim 18, wherein modifying respective frames comprises overwriting luma values of pixels in respective subframes of the sequence of subframes.

20. The computer program product according to claim 18, wherein modifying respective frames comprises overwriting a characteristic of respective subframes in the sequence of subframes, wherein the characteristic is selected from the group consisting of: hue, saturation, and luminance.

* * * * *